United States Patent [19]

Ferguson et al.

[11] 4,341,217
[45] Jul. 27, 1982

[54] BARRIERLESS DISPOSABLE ABSORBENT ARTICLE HAVING AN ABSORBENT CORE ENCASED IN A HOMOGENEOUS OUTER WRAP

[75] Inventors: Susan P. Ferguson; William F. Landrigan, both of Cincinnati, Ohio

[73] Assignee: The Procter & Gamble Company, Cincinnati, Ohio

[21] Appl. No.: 207,165

[22] Filed: Nov. 17, 1980

[51] Int. Cl.³ .............................................. A61F 13/16
[52] U.S. Cl. .............................................. 128/290 W
[58] Field of Search ............ 128/156, 284, 287, 290 R, 128/296

[56] References Cited

U.S. PATENT DOCUMENTS

| | | | |
|---|---|---|---|
| 3,043,301 | 7/1962 | Plantinga et al. | 128/156 |
| 3,060,936 | 10/1962 | Burgeni | 128/290 R |
| 3,067,747 | 12/1962 | Wolterding et al. | 128/290 R |
| 3,881,489 | 5/1975 | Hartwell | 128/287 |
| 3,886,941 | 6/1975 | Duane et al. | 128/290 R |
| 3,929,135 | 12/1975 | Thompson | 128/287 |
| 3,965,906 | 6/1976 | Karami | 128/287 |
| 3,989,867 | 11/1976 | Sisson | 428/132 |
| 4,011,871 | 3/1977 | Taft | 128/284 |
| 4,023,570 | 5/1977 | Chinai et al. | 128/290 R |
| 4,023,571 | 5/1977 | Comerford et al. | 128/290 P |
| 4,026,291 | 5/1977 | Nagano et al. | 128/284 |
| 4,200,103 | 4/1980 | Black et al. | 128/290 W |

Primary Examiner—C. Fred Rosenbaum
Attorney, Agent, or Firm—Richard C. Witte; John M. Pollaro; Fredrick H. Braun

[57] ABSTRACT

An article of manufacture is disclosed for absorbing liquids, particularly body exudates such as menstrual discharges. An absorbent core is encased in a homogeneous outer wrap which may be either unitary or integral. The outer wrap has a specified combination of caliper, apex opening as measured by the maximal diagonal, and a ratio of the apparent caliper to the maximal diagonal of the largest apex opening which impart an ability of the outer wrap to function both as a topsheet portion and as a backsheet portion without the necessity of providing a barrier within the article.

9 Claims, 4 Drawing Figures

BARRIERLESS DISPOSABLE ABSORBENT ARTICLE HAVING AN ABSORBENT CORE ENCASED IN A HOMOGENEOUS OUTER WRAP

BACKGROUND OF THE INVENTION

This invention generally relates to disposable absorbent articles of the type placed against a wearer's body to receive liquids discharged therefrom, and more particularly relates to disposable catamenial pads and the like. Still more particularly, this invention relates to disposable catamenial pads for use between periods of menstruation in which the outer wrap is a homogeneous sheet of material having a multiplicity of protuberances comprising debossments in the topsheet and backsheet portions of the outer wrap. The physical characteristics of the debossments in the topsheet portion and of the debossments in the backsheet portion are substantially similar to each other.

Disposable absorbent articles of the type placed against a wearer's body to receive liquids discharged therefrom are well-known in the prior art and have many uses. For example, disposable diapers are intended to absorb and contain urine; bandages are intended to absorb and contain blood and other body exudates; catamenial pads are intended to absorb and contain menstrual fluids; while pantiliners are intended primarily to absorb and contain vaginal discharges other than menstrual fluids. In each instance, the disposable absorbent article absorbs and contains a liquid, thereby preventing that liquid from soiling, wetting, or otherwise contaminating the vicinity surrounding the point of liquid discharge.

In general, disposable absorbent articles all have the same basic structure which comprises an absorbent core encased in an outer wrap. Frequently, the prior art outer wraps have a liquid permeable user contacting topsheet and a liquid impermeable backsheet. The materials taught in the prior art for use as topsheets have characteristics which permit liquid to rapidly penetrate their thickness while materials which retard the flow of liquid are suggested for use as backsheets.

Because the topsheet and the backsheet components of the outer wrap require liquid handling characteristics which are different from each other, the prior art absorbent articles typically have topsheets and backsheets which are manufactured from materials having different physical characteristics. For example, U.S. Pat. No. RE 26,151 entitled "Disposable Diaper" which issued to R. C. Duncan et al. on Jan. 31, 1967, teaches a disposable absorbent article having a topsheet which is a hydrophobic paper or non-woven fabric web while the backsheet is a polyethylene web.

There have been numerous patents issued which are directed to improving the characteristics of various materials so that they will function better either as a topsheet or as a backsheet. For example, U.S. Pat. No. 3,929,135 entitled "Absorptive Structure Having Tapered Capillaries" which issued to H. A. Thompson on Dec. 30, 1975, teaches a topsheet of liquid impervious material provided with tapered capillaries. The tapered capillaries are sized so as to promote rapid liquid penetration through the topsheet thereby presenting a dry surface feel to the user. U.S. Pat. No. 3,881,489 entitled "Breathable Liquid Impervious Backsheet For Absorptive Devices" which issued on May 6, 1975 to E. W. Hartwell and U.S. Pat. No. 3,989,867 entitled "Absorptive Devices Having Porous Backsheet" which issued to J. B. Sisson on Nov. 2, 1976, both teach backsheets for absorptive devices which permit the passage of air and vapor but act as a barrier to the passage of liquid.

By using materials having different physical characteristics for the topsheet and backsheet components of the outer wrap, the liquid handling characteristics of each may be optimized. In some manufacturing methods and for some product applications, however, it is desirable to use the same, or substantially the same material for both the topsheet and backsheet components.

In those prior art disposable absorbent articles which utilize a homogeneous outer wrap, a separate liquid barrier is provided. This barrier may take the form of a treatment of a portion of the outer wrap. Alternatively, as taught in U.S. Pat. No. 4,200,103 entitled "Increasing Absorbent Capacity of Sanitary Napkin By Sealing Cover Material To Repellant Barrier" which issued to Black et al. on Apr. 29, 1980, a liquid impervious barrier sheet may be introduced to serve the function of the liquid impervious backsheet.

The disposable absorbent articles of the prior art lack the aspects of the present invention whereby a barrierless disposable absorbent article is provided, comprising a homogeneous sheet of material wrapped around an absorbent core.

It is, therefore, an object of the present invention to provide a barrierless disposable absorbent article having a homogeneous outer wrap.

It is another object of the present invention to provide a barrierless disposable absorbent article having a homogeneous outer wrap in which the debossments in the topsheet portion are substantially similar to the debossments in the backsheet portion.

It is a further object of the present invention to provide a barrierless disposable absorbent article having a homogeneous outer wrap in which the debossments are configured so as to be suitable for use in either the topsheet portion or the backsheet portion of the outer wrap.

These and other objects of the invention will be more readily apparent when considered in reference to the following description and when taken in connection with the accompanying drawings.

SUMMARY OF THE INVENTION

According to the present invention, a barrierless disposable absorbent article, such as a catamenial pad, is manufactured such that an absorbent core is encased in a homogeneous outer warp which may be either a single unitary piece of material or a multiplicity of pieces of material affixed together to form an integral outer wrap. The material used to manufacture the outer wrap is liquid impermeable such as polyethylene films, or such as woven or non-woven sheets treated with a binder or the like to be liquid impermeable.

The outer wrap is provided with a multiplicity of protuberances projecting from the plane of the outer wrap toward the absorbent core and having a base in the plane of the outer wrap and an apex remote therefrom. Both the apex and the base of each debossment are apertured.

The outer wrap has a wearer contacting topsheet portion and, opposed thereto, a backsheet portion. The debossments in the topsheet portion are substantially similar to the debossments in the backsheet portion.

DESCRIPTION OF THE PREFERRED EMBODIMENT

Figure 1:
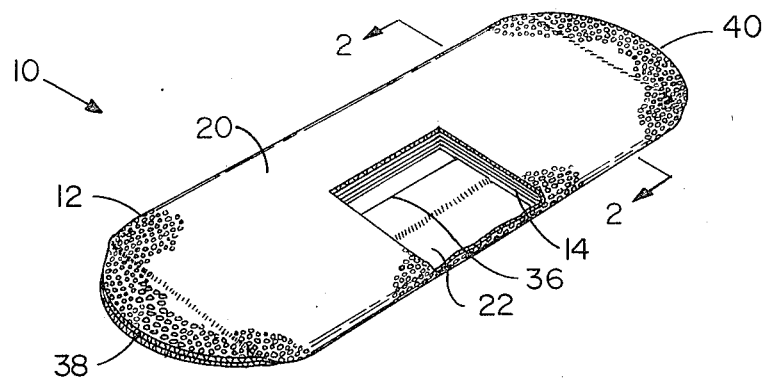
FIG. 1 is a partially cutaway perspective view of a catamenial pad incorporating the features of the present invention.

Referring now to the drawings, there is shown a preferred embodiment of the present invention as it would be used in a disposable absorbent article of the type placed against a wearer's body to receive liquid discharged therefrom and in particular as it would be used in a catamenial pad. It should be understood, however, that the present invention is also applicable for use in other disposable absorbent articles such as diapers, bandages, bedpads, and the like. As used herein, the term "disposable absorbent article" refers to articles intended to absorb and retain liquid and in particular those articles which are placed against or in proximity to the wearer's body to absorb and contain the various liquids discharged from the body (e.g., blood, menses, urine), and further, which articles are intended to be discarded after a single use (i.e., they are not intended to be laundered or otherwise restored and then reused). A catamenial pad is a disposable absorbent article which is worn by females external to the urogenital region and which is intended to absorb and contain menstrual fluids and other vaginal discharges.

As used herein, the term catamenial pad includes absorbent articles, sometimes referred to as pantiliners, which are worn by females external to the urogenital region, between periods of heavy menstrual flow, and which are intended to absorb light menstrual or nonmenstrual discharges. The primary difference between catamenial pads used during periods of heavy menstrual flow and catamenial pads used between periods of heavy menstrual flow (i.e., pantiliners) being the absorbent capacity of the article.

Figure 2:
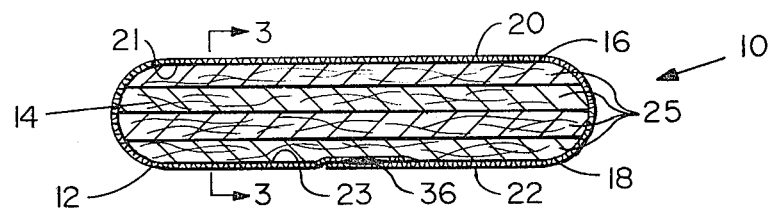
FIG. 2 is a cross-sectional view of the catamenial pad of FIG. 1 taken along line 2—2.

FIG. 1 is a partially cutaway perspective view of a catamenial pad 10 incorporating the present invention. As best seen in FIG. 2, however, the catamenial pad 10 basically comprises an outer wrap 12 and an absorbent core 14. The absorbent core 14 has first and second opposed surfaces 16 and 18, respectively, while the outer wrap 12 comprises a topsheet portion 20 and a backsheet portion 22. The outer wrap 12 encases the absorbent core 14 such that the topsheet portion 20 overlays the first opposed surface 16 and the backsheet portion 22 overlays the second opposed surface 18. Further, the outer wrap 12 has a topsheet inner surface 21 which is in face to face relationship with the first opposed surface 16 of the absorbent core 14 and a backsheet inner surface 23 which is in the face to face relationship with the second opposed surface 18 of the absorbent core 14.

The disposable absorbent article of the present invention is barrierless. As used herein, the term "barrierless" refers to disposable absorbent articles which have an uninterrupted liquid flow path from the topsheet inner surface 21 to the backsheet inner surface 23. Thus, liquid will readily flow from the topsheet inner surface 21 to the backsheet inner surface 23.

The absorbent core 14 is generally compressible, conformable, and nonirritating to the wearer's body. The absorbent core 14 may be manufactured in a wide variety of sizes and from a wide variety of absorbent materials such as comminuted wood pulp generally referred to as airfelt, which are commonly used in disposable absorbent articles and which are capable of absorbing and retaining liquids. Other materials can also be used for the absorbent core 14 such as a multiciplicity of plys of creped cellulose wadding, absorbent foams, or any equivalent material. The absorbent capacity of the absorbent core 14 should, however, be compatible with the expected liquid loading in the intended use of the absorbent article.

In a preferred embodiment of the catamenial pad 10 intended for use as a pantiliner, the absorbent core 14 is preferably thin and flexible to minimize discomfort during wearing and is intended to receive up to about 5 ml. of nonmenstrual vaginal discharges. Accordingly, four sheets 25 of an absorbent web of papermaking fibers having a basis weight of about 16 pounds/3,000 square feet and a caliper off about 0.013 inches (0.03 cm) per sheet are suitable for the absorbent core 14. In the preferred embodiment four such sheets 25 manufactured in general accordance with the procedure set forth in U.S. Pat. No. 3,301,746 which issued to L. H. Sanford et al. on Jan. 31, 1967, were used to manufacture the absorbent core 14.

The shape and dimensions of the absorbent core 14 are selected to fit the urogenital region of wearers of the catamenial pad 10. While the shape and dimensions of the absorbent core 14 may be varied, it has been found that a generally rectangular shaped absorbent core 14 having a length of about 4.5 inches (11.4 cm) a width of about 2.0 inches (5.1 cm) and a caliper of about 0.065 inches (0.165 cm) provides satisfactory results for many wearers. However, other dimensions and even other shapes (e.g., hour glass) may also be used for the absorbent core 14.

The outer wrap 12 is preferably compliant, soft feeling, nonirritating to the wearer's body and is manufactured from a liquid impermeable material. Alternatively, the outer wrap 12 may be manufactured from a liquid permeable material, such as a nonwoven web, which has been coated or otherwise treated to be liquid impermeable. There are many suitable materials from which the outer wrap 12 may be manufactured. Polymeric films are, however, preferred with polyethylene films being most preferred.

In the preferred embodiment illustrated in FIGS. 1 and 2, the outer wrap 12 is a unitary sheet of material having a first and a second end flap 38 and 40, respectively, (FIG. 1). As used herein the term "unitary" refers to outer wraps 12 which are formed from a single homogeneous piece of material which is neither divided nor discontinuous. The outer wrap 12 is wrapped around the absorbent core 14 and is affixed to itself along a seam 36 which is adjacent to the second opposed surface 18 and which traverses the catamenial pad 10 longitudinally. The first and second end flaps 38 and 40, respectively, extend beyond the ends of the absorbent core 14 and are sealed so as to completely encase the absorbent core 14 within the outer wrap 12. The portion of the outer wrap 12 overlaying the first opposed surface 16 is the topsheet portion 20 of the outer wrap 12 and the portion of the outer wrap 12 overlaying the second opposed surface 18 is the backsheet portion 22 of the outer wrap 12.

Figure 3:
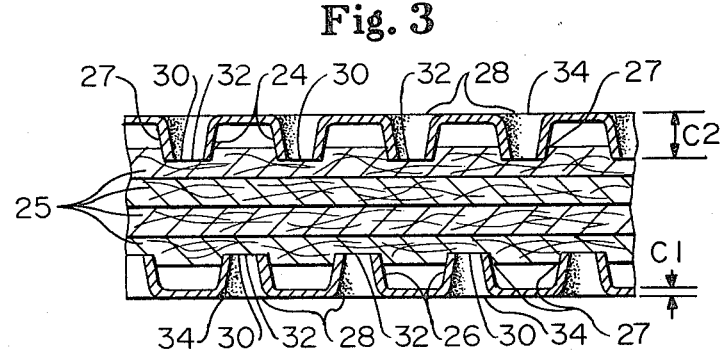
FIG. 3 is a greatly enlarged cross-sectional view of the catamenial pad of FIG. 2 taken along line 3—3.

Referring now to FIG. 3, it can be seen that the outer wrap 12 is provided with a multiplicity of protuberances 27 projecting from the plane of the outer wrap 12 inwardly toward the absorbent core 14. The plane of the outer wrap 12 is that plane passing through the surface of the outer wrap 12 which faces outwardly from the absorbent core 14. The protuberances 27 in the topsheet portion 20 are topsheet debossments 24 and the protuberances 27 in the backsheet portion 22 are backsheet debossments 26.

The protuberances 27 each have a base 28 in the plane of the outer wrap 12 and an apex 30 remote therefrom. The apex 30 has an apex opening 32 and the base 28 has a base opening 34.

The base openings 34 and the apex openings 32 may have a variety of shapes. For example, the base and apex openings 34 and 32, respectively, may be circular, elliptical or even irregularly shaped. The base openings 34 and the apex 32 preferably are uniform having the same shape and dimensions. It is, however, also alternatively preferred to provide the base openings 34 and the apex openings 32 with shapes and/or dimensions which are different from each other.

Each base opening 34 and each apex opening 32 has a maximal diagonal. For rectilinear shapes the maximal diagonal is the longest line that can be drawn between two nonadjacent vertices of the shape. For curvilinear shapes, the maximal diagonal is the largest diameter of the shape. Outer wraps 12 have a largest apex opening 32 which is the apex opening 32 having the largest maximal diagonal.

The maximal diagonal for the base openings 34 may be equal to the maximal diagonal for the apex opening 32 forming parallel walled protuberances 27 or the base opening 34 may have a maximal diagonal larger than the maximal diagonal of the corresponding apex opening 32 thereby forming tapered protuberances 27.

Irrespective of the shape, dimensions, or uniformity of the base and apex openings 34 and 32, the outer wrap 12 is homogeneous. As used herein the term "homogeneous" refers to outer wraps 12 in which any representative portion thereof is substantially similar to any other representative portion. Accordingly, the physical characteristics (percent open area, size, shape and maximal diagonal of the base openings, size, shape, and maximal diagonal of the apex opening, caliper, etc.) of the topsheet debossments 24 in a representative sample of the topsheet portion 20 will be substantially similar to the physical characteristics of the backsheet debossments 26 in a representative sample of the backsheet portion 22.

Preferably, the maximal diagonal of the largest apex opening 32 is from about 0.01 inches to about 0.10 inches (about 0.025 cm to about 0.25 cm) and is most preferably from about 0.01 inches to about 0.04 inches (about 0.025 cm to about 0.10 cm). The maximal diagonal of the largest apex opening 32 is readily determined using, for example, a 150 power microscope having a calibrated eyepiece. In this manner, the largest apex opening 32 may be identified visually and its maximal diagonal determined by reading directly from the calibrated eyepiece. If the apex openings 32 are all of the same size and are circular as shown in the drawings of the preferred embodiment, the maximal diagonal of the largest apex opening 32 is easily determined by visually measuring the diameter of any apex opening 32.

The protuberances 27 may be formed using any of the several different methods that are well known in the art. For example, a suitable method and apparatus is disclosed in U.S. Pat. No. 4,151,240 entitled Method of and Apparatus for Debossing and Perforating a Running Ribbon of Thermoplastic Film which issued to M. B. Lucas et al. on Apr. 24, 1979 which patent is incorporated herein by reference.

The outer wrap 12 has a true caliper C1 and an apparent caliper C2. The true caliper C1 is the thickness of the material used for the outer wrap 12 before the protuberances 27 are formed therein. The apparent caliper, C2, is the in use thickness of the outer wrap 12 after the protuberances 27 have been formed and is measured from the base 28 to the apex 30 of the protuberance 27. The apparent caliper is preferably between about 0.013 inches (0.033 cm) and about 0.035 inches (0.089 cm) and most preferably between about 0.017 inches (0.043 cm) and about 0.025 inches (0.064 cm). To simulate the loads encountered by the outer wrap 12 in use the caliper measurements are made with the outer wrap 12 subjected to a compressive force of about 0.209 psi (14.4 kilopascals). Accordingly, the apparent caliper C2 may be determined using any suitable procedure which will determine the thickness of the outer wrap 12 under the required compressive force. For example, a motorized micrometer such as manufactured by Testing Machines, Inc. of Mineola, N.Y. and marketed under the tradename Model 549 may be used.

In use the catamenial pad 10 is placed against the body of the wearer with the topsheet portion 20 in contact with the wearer's skin. The catamenial pad 10 may be held in place against the body using any of the methods well known in the art such as by affixing the catamenial pad 10 to the wearer's undergarments. This may be conveniently done by applying an adhesive to the backsheet portion 22 as is well known in the art.

Liquid is discharged onto and passes through the topsheet portion 20 before being absorbed by the absorbent core 14. Because the outer wrap 12 is manufactured from a liquid impermeable material, the liquid can pass through the topsheet portion 20 only by passing through the topsheet debossments 24. That is, lateral wicking in the plane of the material does not occur in liquid impermeable materials. Rapid penetration through the thickness of the topsheet portion 20 by the liquid is desirable to prevent the liquid from running across the surface of the topsheet portion 20 and leaking off the sides of the catamenial pad 10.

The rate at which liquid penetrates through the thickness of the topsheet portion 20 is measured by the strikethrough time. The lower the strikethrough time the faster the liquid will penetrate the thickness of the topsheet portion 20. It has been found that materials having strikethrough times, determined in accordance with the procedures hereinafter set forth, of less than about 80 seconds and preferably less than about 30 seconds are satisfactory for use as outer wraps 12.

After passing through the topsheet portion 20 the liquid is absorbed by the absorbent core 14. The absorbed liquid wicks through the thickness and toward the periphery of the absorbent core 14 eventually reaching the backsheet inner surface 23 of the outer wrap 12. Since the catamenial pad 10 is barrierless, the liquid does not encounter any retarding obstacle which prevents it from reaching the backsheet inner surface 23. To prevent the liquid from wetting the vicinity surrounding the catamenial pad 10, it is desirable that the backsheet portion 22 retard liquid flow from the absorbent core 14 through the thickness of the backsheet portion 22.

The amount of liquid which passes from the absorbent core 14 through the backsheet portion 22 is the bleed through quantity. The lower the bleedthrough quantity of a material the more effective that material will be in retarding liquid flow. It has been found that materials have bleed-through quantities, as determined in accordance with the procedures hereinafter set forth, of less than about 0.075 grams are satisfactory for use as outer wraps 12.

From the foregoing, it is clear that the topsheet portion 20 preferably has characteristics which permit liquid to rapidly penetrate its thickness from the outer surface to the absorbent core 14 while the backsheet portion 22 preferably has characteristics which retard liquid flow from the absorbent core 14 to the outer surface of the backsheet portion 22. The present invention provides these preferred characteristics for both the topsheet portion 20 and the backsheet portion 22 by using a homogeneous outer wrap 12.

An outer wrap 12, which is homogeneous and has: a minimum apparent caliper (C2) of from about 0.013 inches (0.033 cm) to about 0.035 inches (0.089 cm); a largest apex opening 32 having a maximal diagonal of from about 0.01 inches (0.025 cm) to about 0.10 inches (0.025 cm); and a ratio of the apparent caliper (C2) to the maximal diagonal of the largest apex opening 32 of at least about 0.35 will have both strikethrough and bleedthrough characteristics which are satisfactory.

The strikethrough time of a sample of the topsheet portion 20 may be determined using any suitable procedure which will measure the time required for a quantity of liquid to pass through the sample of the topsheet portion 20. The following procedure was used to generate the data presented in Table I.

A 4 inch×4 inch (10 cm.×10 cm.) sample of the topsheet portion 20 is placed over an absorbent core which has preferably been conditioned or stored at 73° F. (24° C.) and 50% relative humidity to help eliminate variations in the data due to varying moisture contents of the absorbent cores. The absorbent core of each test sample is comminuted woodpulp weighing from 2.4 to 3.0 grams with a density of from 0.7 to 0.85 grams per cubic centimeter. A 4 inch×4 inch (10 cm.×10 cm.) plate weighing 800 grams and having a 0.25 inch (6.3 millimeter) diameter hole centered therein is placed on the sample. The hole traverses the thickness of the plate and is filled with 5 milliliters of a menstrual fluid simulating liquid having a surface tension of about 70 dynes. The time required for the 5 milliliters of liquid to penetrate the sample is the strikethrough time. The shorter the strikethrough time the better the strikethrough characteristic of the sample.

The bleed through quantities presented in Table I were generated using the following procedure. A 1 square inch (6.5 sq. cm) piece of absorbent material is centered on a 2 square inch (25.8 sq. cm) sample of the backsheet inner surface 23 of the outer wrap 12. Four sheets of a web of papermaking fibers weighing about 0.016 gms/sheet such as is manufactured by The Procter & Gamble Company, Cincinnati, Ohio and marketed under the tradename "Bounty" was used for the absorbent material. Five milliliters of a liquid having a surface tension of 70 dynes is introduced onto the center of the absorbent material and a 0.25 psi (1.7 kilopascals) pressure applied to the absorbent material.

After 1 minute, an absorbent paper such as is manufactured by Whatman Limited and marketed under the tradename Ashless 44 which has been preweighed, is inserted between the sample of the outer wrap 12 and the surface on which the test is being conducted. After waiting another 1 minute, the pressure is removed and the absorbent paper weighed. The increase in the weight of the absorbent paper is the bleedthrough quantity.

As can be seen in Table I, Samples A, B, and C each have an apparent caliper (C2), a maximal diagonal of the largest apex opening 32 and a ratio of apparent caliper (C2) to the maximal diagonal of the largest apex opening 32 within the limits as hereinbefore set forth. Samples A, B, and C each have both a strikethrough time of less than 80 seconds and a bleedthrough quantity of less than 0.075 grams.

Samples D, E, F and G have bleedthrough quantities greater than 0.075 grams. Samples D and E each had a ratio of apparent caliper (C2) to maximal diagonal of the largest apex opening 32 less than 0.35 while samples F and G each had apparent calipers less than 0.013 inches.

TABLE I

Strikethrough Times and Bleedthrough Quantities For Various Outer Wraps

| Sample | Apparent Caliper (C2) (Inches) Topsheet Portion/ Backsheet Portion |
|---|---|
| A(1) | 0.0172/0.0172 |
| B(2) | 0.0205/0.0206 |
| C(3) | 0.0165/0.0170 |
| D(3) | 0.0159/0.0165 |
| E(3) | 0.0105/0.0136 |
| F(3) | 0.0112/0.0108 |
| G(3) | 0.0096/0.0096 |

| Sample | Maximal Diagonal of the Largest Apex Opening (Inches) Topsheet Debossments/ Backsheet Debossments | Ratio of the Apparent Caliper to the Maximal Diagonal of the Largest Apex Opening (dimensionless) Topsheet Debossments/ Backsheet Debossments |
|---|---|---|
| A | 0.031/0.031 | 0.55/0.55 |
| B | 0.022/0.022 | 0.93/0.94 |
| C | 0.042/0.042 | 0.39/0.40 |
| D | 0.055/0.055 | 0.29/0.30 |
| E | 0.098/0.098 | 0.11/0.14 |
| F | 0.023/0.023 | 0.49/0.47 |
| G | 0.017/0.017 | 0.56/0.56 |

| Sample | Strikethrough Time (Sec.) | Bleedthrough Quantity (Gms) |
|---|---|---|
| A | 28.11 | 0.019 |
| B | 28.56 | 0.003 |
| C | 18.82 | 0.040 |
| D | 22.38 | 0.091 |
| E | 26.33 | 0.143 |
| F | 46.16 | 0.115 |
| G | 32.43 | 0.138 |

NOTES
(1)The outer wrap 12 was a polyethylene film having irregularly shaped rectilinear protuberances 27 in which the maximal diagonal of the apex opening 32 was essentially equal to the maximal diagonal of the base opening 34.
(2)The outer wrap 12 was a polyethylene film having circular protuberances 27 in which the maximal diagonal of the apex opening 32 was smaller than the maximal diagonal of the base opening 34. All protuberances were essentially of the same shape and dimensions.
(3)The outer wrap 12 was a polyethylene film having circular protuberances 27 in which the maximal diagonal of the apex opening 32 was essentially equal to the maximal diagonal of the base opening 34. All protuberances 27 were essentially of the same shape and dimensions.

Figure 4:
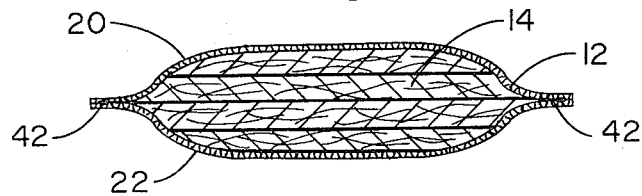
FIG. 4 is a cross-sectional view of an alternative embodiment of the present invention taken along line 2—2.

It will be understood that the foregoing description is of a preferred embodiment of the invention and is therefore merely representative. Obviously, there are many variations and modifications of the present invention in light of the preceding teaching. As shown in FIG. 4, for example, the outer wrap 12 may be of an integral construction. As used herein, the term integral refers to outer layers 12 which are formed from two or more pieces of material which are affixed to each other. Accordingly, the topsheet portion 20 is affixed to the backsheet portion 22 along outer seam 42, thereby encasing the absorbent core 14.

What is claimed is:

1. A barrierless disposable absorbent article comprising a thin, flexible absorbent core means for absorbing and retaining liquid, said absorbent core means having first and second opposed surfaces; and a homogeneous outer wrap having a topsheet portion and a backsheet portion, said outer wrap encasing said absorbent core means with said topsheet portion overlaying said first opposed surface and said backsheet portion overlaying said second opposed surface, said homogeneous outer wrap having an apparent caliper and having a multiplicity of protuberances projecting inwardly towards said absorbent core means, each of said protuberances having a base and having an apex remote from said base, said base having a base opening and said apex having an apex opening, said outer wrap having a largest apex opening; the ratio of the apparent caliper of said outer wrap to the maximal diagonal of said largest apex opening being at least about 0.35 and the apparent caliper of said homogeneous outer wrap being from about 0.013 inches to about 0.035 inches.

2. The barrierless disposable absorbent article of claim 1 wherein the apparent caliper of said homogeneous outer wrap is from about 0.017 inches to about 0.025 inches.

3. The barrierless disposable absorbent article of claim 1 or 2 wherein the maximal diagonal of said largest apex opening is from about 0.01 inches to about 0.10 inches.

4. The barrierless disposable absorbent article of claim 1 or 2 wherein the maximal diagonal of said largest apex opening is from about 0.01 inches to about 0.04 inches.

5. The barrierless disposable absorbent article of claim 3 wherein said homogeneous outer wrap is unitary.

6. The barrierless disposable absorbent article of claim 3 wherein said homogeneous outer wrap is integral.

7. A barrierless pantiliner comprising a thin, flexible abosrbent core means for absorbing and retaining liquid, said absorbent core means having first and second opposed surfaces; and a homogeneous outer wrap having a topsheet portion and a backsheet portion, said outer wrap encasing said absorbent core means with said topsheet portion overlaying said first opposed surface and said backsheet portion overlaying said second opposed surface, said homogeneous outer wrap having an apparent caliper and having a multiplicity of protuberances projecting inwardly toward said absorbent core means, each of said protuberances having a base and having an apex remote from said base, said base having a base opening and said apex having an apex opening, said outer wrap having a largest apex opening; the ratio of the apparent caliper of said homogeneous outer wrap to the maximal diagonal of said largest apex opening being at least about 0.35 and the apparent caliper of said homogeneous outer wrap being from about 0.013 inches to about 0.035 inches.

8. The barrierless pantiliner of claim 7 wherein said largest apex opening has a maximal diagonal of from about 0.01 inches to about 0.10 inches.

9. The barrierless pantiliner of claim 8 wherein an adhesive means for attaching said outer wrap to the wearer's garments is affixed to said backsheet portion.

* * * * *